(12) United States Patent
Rusko et al.

(10) Patent No.: US 8,229,188 B2
(45) Date of Patent: Jul. 24, 2012

(54) SYSTEMS, METHODS AND APPARATUS AUTOMATIC SEGMENTATION OF LIVER IN MULTIPHASE CONTRAST-ENHANCED MEDICAL IMAGES

(75) Inventors: Laszlo Rusko, Szolnok (HU); Gyorgy Bekes, Szeged (HU); Marta Fidrich, Szeged (HU)

(73) Assignee: General Electric Company, Schenectady, NY (US)

( * ) Notice: Subject to any disclaimer, the term of this patent is extended or adjusted under 35 U.S.C. 154(b) by 1132 days.

(21) Appl. No.: 11/871,352

(22) Filed: Oct. 12, 2007

(65) Prior Publication Data

US 2009/0097726 A1 Apr. 16, 2009

(51) Int. Cl.
*G06K 9/00* (2006.01)

(52) U.S. Cl. ............. 382/128; 382/131; 382/134

(58) Field of Classification Search .......... 382/128–134, 382/156, 173, 274; 600/458, 437, 420
See application file for complete search history.

(56) References Cited

U.S. PATENT DOCUMENTS

| 7,545,979 B2* | 6/2009 | Fidrich et al. ................. 382/173 |
| 2003/0016850 A1* | 1/2003 | Kaufman et al. ............. 382/128 |
| 2006/0052690 A1* | 3/2006 | Sirohey et al. ............... 600/420 |
| 2006/0228009 A1 | 10/2006 | Fidrich et al. |
| 2007/0206880 A1* | 9/2007 | Chen et al. ................... 382/294 |

OTHER PUBLICATIONS

Lamecker et al (Segmentation of the liver using a 3D Statistical Shape Model 2004, http://www.zib.eu/Publications/Reports/ZR-04-09.pdf.*

Saddi et al (Region Based Segmentation via Non-Rigid Templates matches Oct. 2007, IEEE 22th Internationa Conference on COmputer Vision 2007, ICCV 2007, pp. 1-7.*

Luc Soler (PHD), Nerve Delingette(PHD), Gregoire Malandain (PHD), Johan Montagnat (PHD), Nicholas Ayache (PHD), Christophe Koehl (E), Olivier Dourtheb(MD), Benoit Malassagne (MD), Michelle Smith (MD), Didier Mutter (MD, PHD), Jacques Marescaux(MD), "Fully automatic anatomical, pathological, and functional segmentation from CT scans for hepatic surgery," Proc. SPIE vol. 3979, p. 246-255, Medical Imaging 2000.

Hans Lamecker, Thomas Lange, Martin Seebass, "Segmentation of the Liver using a 3D Statistical Shape Model," Konrad-Zuse-Zentrum für Informationstechnik Berlin, ZIB-Report 04-09 (Apr. 2004).

"National Library of Medicine Insight Segmentation and Registration Toolkit", retrieved from http://www.itk.org/ on Jul. 3, 2007.

Yonggang Shi, William Clem Kar, "A fast implementation of the level set method without solving partial differential equations," Boston University, Department of Electrical and Computer Engineering, Jan. 2005.

(Continued)

*Primary Examiner* — Vikkram Bali
*Assistant Examiner* — Nancy Bitar
(74) *Attorney, Agent, or Firm* — The Small Patent Law Group; Dean D. Small

(57) ABSTRACT

Systems, method and apparatus in which some embodiments of automatic segmentation of a liver parenchyma from multiphase contrast-enhanced computed-tomography images includes analyzing an intensity change in the images belonging to the different phases in order to determine the region-of-interest of the liver, thereafter segmenting starting from the region-of-interest and incorporating anatomical information to prevent oversegmentation, and thereafter combining the information of all available images.

20 Claims, 15 Drawing Sheets
(8 of 15 Drawing Sheet(s) Filed in Color)

OTHER PUBLICATIONS

Vicent Caselles, Ron Kimmel, Guillermo Sapiro, "Geodesic Active Contours," International Journal of Computer Vision 22(1), 61-79 (1997), retrieved from http://www.iua.upf.es/~vcaselles/papers_v/GAC_artical.pdf on Jul. 3, 2007.

Pohle, Regina; Toennies, Klaus D. "Segmentation of medical images using adaptive region growing," Proc. SPIE vol. 4322, p. 1337-1346, Medical Imaging 2001: Image Processing, Milan Sonka; Kenneth M. Hanson, Eds. retrieved from http://wwwisg.cs.uni-magdeburg.de/bv/pub/pdf/mi_4322_153.pdf on Jul. 3, 2007.

"Neighborhood Connected Image Filter" retrieved from http://www.itk.org/Doxygen/html/classitk_1_1NeighborhoodConnectedImageFilter.html on Jul. 3, 2007.

Chen Xiaohua et al., MICCAI 2004, "Simultaneous Segmentation and Registration for Medical Image" pp. 663-670, Springer-Verlag Berlin Heidelberg.

Killian M. Pohl et al., "A Unifying Approach to Registration, Segmentation and Intensity Correction", MICCAI 2005, LNCS 3749, pp. 310-318, Springer-Verlad Berlin Heidelberg.

Jung-Ha An et al., MICCAI 2005, LNCS 3749, "A Variational PDE based Level Set Method for a Simultaneous Segmentation and Non-rigid Registration", pp. 286-293, Springer-Verlag.

Jeff Dicker, "Fast Marching Methods and Level Set Methods," The University of British Columbia Okanagan Campus, Mar. 2006.

Sethian, J. A., "Level Set Methods and Fast Marching Methods: An implementation," Cambridge University Press, New York, 2006.

\* cited by examiner

SYSTEMS, METHODS AND APPARATUS AUTOMATIC SEGMENTATION OF LIVER IN MULTIPHASE CONTRAST-ENHANCED MEDICAL IMAGES

FIELD OF THE DISCLOSURE

This disclosure relates generally to healthcare imaging systems, in particular to imaging of livers in human patients.

BACKGROUND

Computer assisted planning of liver treatments is primarily implemented using computed tomography (CT). The computer assisted planning can be an important aid for surgery decisions and visualization of individual patient anatomy in three dimensions (3D). The liver treatments include minimally invasive therapies, oncology liver sectioning, and living donor transplantation.

The computer assisted planning of liver treatments is based on the liver volume, the anatomical liver segments, the vessel structure, and the relation of lesions to these structures. Detection of boundaries between liver segments is the first step of the preoperative planning. Radiologists currently use CT images with intravenous contrast infusion, in order to detect lesions and vessels in the liver. The key point of the above-mentioned treatments is the liver volume segmentation.

There are several published methods about segmentation of CT images. Most of these CT image segmentation methods are some variants of the region growing, active contour/surface, level-set, thresholding and/or classification algorithms. In addition, the CT image segmentation methods are often based on a statistical, anatomical, or geometric model.

Unfortunately, only a few CT image segmentation methods having been tested clinically. In most cases, CT segmentation methods are merely simulated with none or very little patient data. Usually—with a few exceptions—"general organ segmentation methods" are disclosed that are intended to segment "every organ" in "every modality." However, very little statistical evaluation information is available on the general organ segmentation methods is available. Thus, the reliability and effectiveness of the general organ image segmentation methods are highly doubtful.

Some conventional methods to automatically segment the liver image from contrast-enhanced CT image scans delineate the skin, bones, lungs, kidneys and spleen, by combining the use of thresholding, mathematical morphology and distance maps before extracting an image of the liver. In these conventional methods, a 3D reference model is generated from manually segmented image of a liver and adjusted onto the image with rigid and affine registration. The 3D reference model is deformed to get the final result. The weakness of these conventional methods is that only one phase of the contrast-enhanced examination is used, which is acquired according to a special protocol and does not correspond to the general practice.

Other conventional methods of segmenting an image of a liver from a CT image that also use a 3D statistical shape model include an iterative technique that first builds a statistical model from a training set of shapes. Each shape is given by M points sampled on its surface. The points must correspond in an anatomically meaningful way, and the coordinates must be given relative to a common reference frame. The next step is positioning a mean shape into the image data. At each iteration, several position adjustments are performed until no further significant improvement is achieved. Then single shape adjustment is applied. Unfortunately, no clinical evaluation of this method has been performed.

The level-set methods are other conventional methods of organ segmentation. One advantage of the level-set methods is that topological changes are managed and the problem is defined in one higher dimension. The main disadvantage is that all level-set methods are very time-consuming and produce leakage.

An active-contour method is used in clinical to segment abdominal organs. The active-contour method works well on native images, because the organs are homogenous. In case of contrast-enhanced images, the contrast agent is cumulated differently in different parts of the liver. For example the vessels and some tumors will have greater intensity values than the liver parenchyma. The active contour method starts from a smaller region and expands the smaller regions to fit the surface to the contour of the organ. The vessels and tumors set back the regular growing of the surface.

A region-growing based approach to segment organ images can be used with good results on contrast-enhanced images. The method starts from a small region (environment of input curve, or point), and every neighboring voxel is added to the actual region, if intensity of the voxel corresponds to a pre-defined range. Region-growing methods can close round the vessels and tumors, but region-growing methods are very sensitive for the input and can easily flow out to other organs that have similar intensities.

BRIEF DESCRIPTION

In one aspect, a liver image is roughly segmented (without registration) using multiphase histogram analysis as a region of interest (ROI). Then, using the ROI, the liver is segmented in each phase separately using an advanced region growing method. Next, the segmented liver volumes (as binary images) are accurately registered to compensate the patient's breathing between the different phases. Thereafter, the result is taken as combination of the registered images.

In another aspect, imaging a liver includes a segmenting an image of a liver roughly in an image using multiphase histogram analysis as a region of interest (ROI), segmenting the liver image in each phase separately using an advanced region growing method, registering the segmented liver volumes to compensate for breathing of the patient between the different phases and combining the registered images in a memory.

In a further aspect, a system comprises a processor, a storage device coupled to the processor including a plurality of representations of multiphase contrast-enhanced computed-tomography images, and software apparatus operative on the processor to perform segmentation of the liver from the representations of multiphase contrast-enhanced computed-tomography images.

Systems, processes, and computer-readable media of varying scope are described herein. In addition to the aspects and advantages described in the brief description, further aspects and advantages will become apparent by reference to the drawings and by reading the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
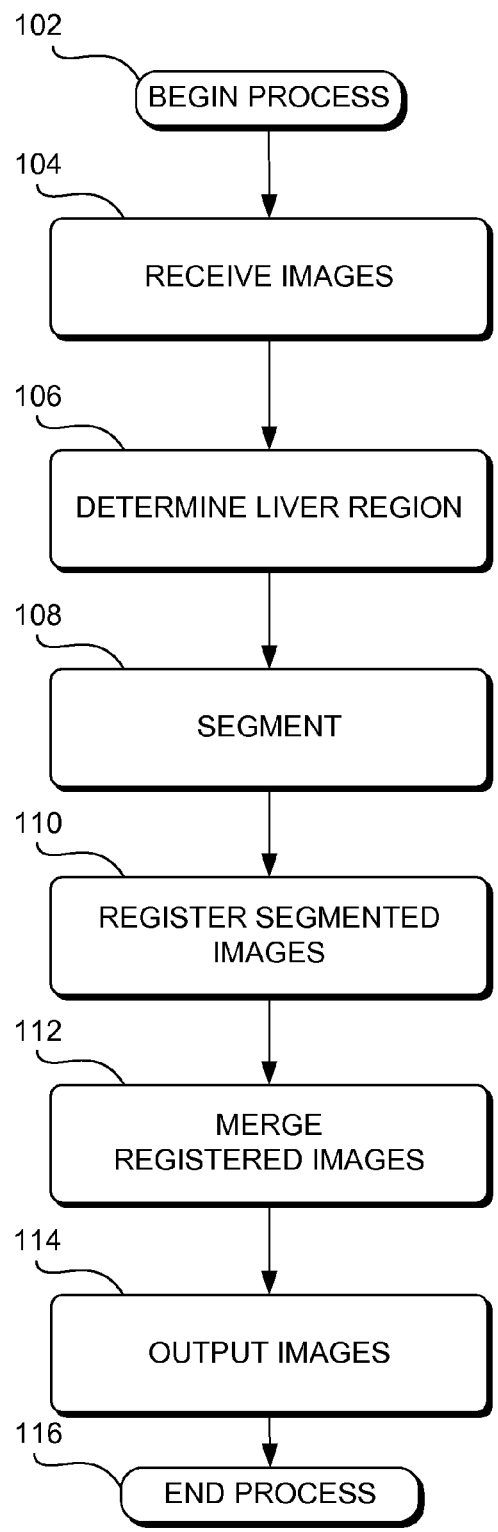
FIG. 1 is a flowchart of a process for generating an image of a liver in a human patient, in accordance with an embodiment.

In the following detailed description, reference is made to the accompanying drawings that form a part hereof, and in which are shown, by way of illustration, specific embodiments that can be practiced. These embodiments are described in sufficient detail to enable those skilled in the art to practice the embodiments, and it is to be understood that other embodiments can be utilized, and that logical, mechanical, electrical and other changes can be made, without departing from the scope of the embodiments.

The detailed description is divided into six sections. In the first section, a system level overview is provided. In the second section, example methods are described. In the third section, images are illustrated. In the fourth section, histograms are discussed. The fifth section discloses hardware and an operating environment, in conjunction with which embodiments can be practiced. The sixth section provides a conclusion which reviews aspects of the subject matter described in the preceding segments of the detailed description. A technical effect of the subject matter described herein includes generating an image in which a liver is visually separated from other organs in the image.

As used herein, the term "Hounsfield Units" or the abbreviation "HU" refers to units employed for mapping effective linear X-ray attenuation coefficients which comprise X-ray or Computer-aided Tomographic (CT) images to a convenient standard numeric scale. Values on this scale are expressed in Hounsfield Units (HU) and are sometimes referred to as CT numbers. On the HU scale, the value of water in a CT image is zero and the value of air is −1000.

As used herein, the term "pixel" means a two-dimensional unit cell or elementary picture element in a display. As used herein, the term "voxel" means a three-dimensional unit cell for representation of three-dimensional data fields. Pixels and voxels have a set of values associated with them.

Segmentation, in the sense used here, involves differentiating between data representing various organs. Segmentation can also include identifying data describing pathological features. Segmentation can be employed to clearly define organs, or for quantification of the size of a lesion. As used herein, the term "segmentation" means the process of partitioning a digital image into multiple regions (sets of pixels), or of partitioning a digital three-dimensional representation into multiple regions (sets of voxels). The goal of segmentation is to simplify and/or change the representation of a dataset into something that is more meaningful and as a way of facilitating analysis and quantification of features of interest. Image segmentation is typically used to locate objects and boundaries (lines, curves, etc.) in images, with similar processes being employed with volumetric data.

The result of segmentation is a set of regions that can collectively cover the entire image or volumetric dataset, or a set of contours extracted from the image or volumetric dataset via edge detection and other conventional signal or image processing techniques. Each of the pixels or voxels in a given region are similar with respect to some characteristic or computed property, such as color, intensity or texture. Adjacent regions are significantly different with respect to the same characteristic(s).

As used herein, the term "phase" is used to distinguish between measurements taken at a time when a specific biological activity is at a specific stage. For example, in case of a contrast-enhanced CT examination of the liver the term "arterial phase" refers to a time when contrast agent is visible primarily in the heart and arteries, whereas the term "venous phase" is used to refer to a time when contrast agent is visible in the portal vein of the liver. Other phases can be defined as corresponding to different portions of the cyclical pumping action of the heart or with reference to other indicia.

As used herein, the term "histogram" refers to a function which assigns a probability to each intensity value. This probability shows the probability of a voxel or pixel to have this intensity. For example, a probability of 0.5 for an intensity of 100 Hounsfield Units means that half of the voxels or pixels have a value of 100 Hounsfield units. Histograms can relate to a single image, or can relate to two or more images.

As used herein, the term "registration" means alignment of features contained in at least portions of two or more images to establish multiple points representative of the same physical feature. In other words, data elements representing corresponding portions of each of two or more datasets are co-located or coordinated to allow meaningful combination of the elements of the two or more datasets.

System Overview

The aspects described and disclosed herein can be implemented via processes such as those described below with reference to FIGS. 1-5. Processes 100-500 of FIGS. 1-5 can be implemented via computer-readable instructions embodied as computer-readable code on a computer-readable medium (such as the memory devices 1450 of FIG. 14, supra) which, when executed by one or more processors (e.g., computer 1430 and/or image processing engine 1435 of FIG. 14) causes the one or more processors to implement the acts described infra with respect to processes 100, in order to segment the liver by combining the information of all available phases of a contrast enhanced CT examination. The datasets can comprise pixel data, voxel data or other representational forms, and can be derived from any of many different types of instruments developed for the purpose of collecting data representative of anatomical (and often internal) aspects of a patient, such as the patient 1412 depicted in FIG. 14.

Segmenting the liver volume is often difficult if only one image is available even if the image is enhanced using some contrast agent. The difficulty of segmentation of liver volume is due to the fact that the liver is surrounded by some organs, the intensity of which can be very similar to the intensity of the liver concerning any of the phases. In general, the method of FIG. 1 combines the information of all available phases of a multiphase contrast-enhanced medical exam. FIG. 1 demonstrates the main actions of the method.

A series of images (a plurality of images) is received and loaded into memory, at block 104.

In the block 106, the region of interest (ROI) of the liver is determined. One example of a process to determine the liver ROI is described in FIG. 2 below.

In the block 108, the liver is segmented in each image separately. One example of a process to segment the liver in each image is described in FIG. 3 below.

In block 110, the segmented images are registered. One example of a process to register the segmented images is described in FIG. 5 below.

Merging registered images is performed at block 112. After all segmented volumes are registered and have the same properties (e.g. resolution, voxel spacing), merging the segmented volumes into a final result is possible. The result can be defined as arbitrary function of the segmented volumes. The simplest function is to take the intersection of all segmented volumes.

Images are output, at block 114. After all segmented volumes are merged, the merged images can be presented to the user, such by displaying the merged images on a screen or printing the image.

Process 100 automatically segments the liver volume. This yields a highly efficient, user-friendly workflow having no need to trace a contour on a starting slice, no need for initial model fitting, no need of manual ROI or slice range selection.

Process 100 can segment the liver volume in semi-automatic mode, using user given initial curve to handle special cases. In process 100, there is no need for a special acquisition protocol, instead, the contrast-enhanced multiphase images produced by the every day clinical routine can be used.

Process 100 can be extended to other modalities and can be adapted to other organs (spleen, heart, etc.). Process 100 is both accurate and precise.

An example of a computer useful in implementing process 100 is described below with reference to FIG. 15.

Methods

Figure 2:
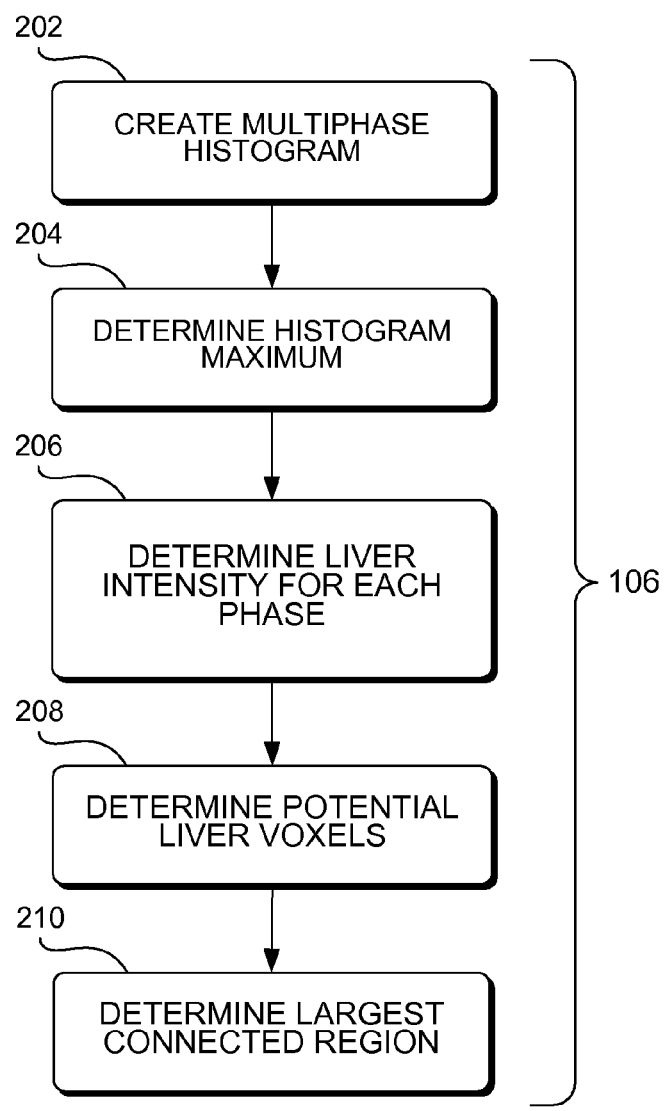
FIG. 2 is a flowchart of a process to determine the liver region-of-interest, according to an embodiment.

FIG. 2 is a flowchart of a process 200 to determine the liver region-of-interest, according to an embodiment. Process 200 is one example of determining the liver region-of-interest 106 in FIG. 1 above.

In determining the liver ROI, a connected 2D region of voxels of that are located inside the liver is identified in all input images. The ROI is based on the analysis of the voxel intensities incorporating the multiphase histogram of the input series. Method 200 includes creating a multiphase histogram based on all available phases (see FIG. 11 for example), at block 202. Thereafter, method 200 includes determining the maximum of the histogram (largest peak of the histogram in FIG. 11), at block 204. The largest peak of the histogram represents the liver in the majority of the cases even if the different phases are only roughly registered (see FIG. 13 for example). Thereafter, method 200 includes determining the intensity of the liver for each phase based on the location of the largest peak, at block 206. Thereafter, method 200 includes potential liver voxels are determined, the intensity of which is equal to the intensity of the liver in all phases, at block 208. Finally, the largest connected component of this voxel set is determined, that is used as ROI, at block 210. The more phases that are available, the more reliable result is provided by the automatic ROI detection. Note that user can initialize the segmentation manually, if the liver region cannot be determined automatically in very unusual cases.

Figure 3:
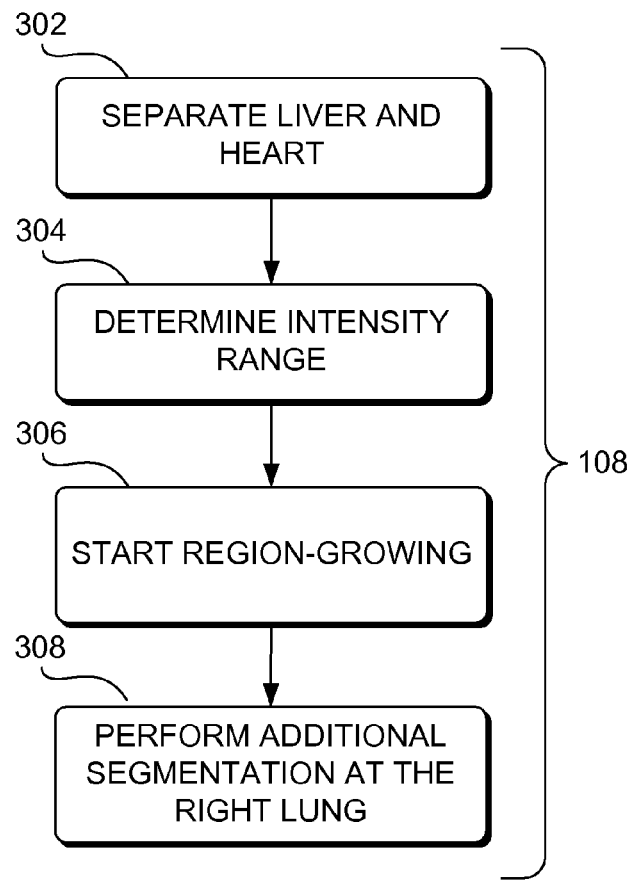
FIG. 3 is a flowchart of a process to segment the liver in each image, according to an embodiment.

FIG. 3 is a flowchart of a process 300 to segment the liver in each image, according to an embodiment. Process 300 is one example of segmenting the liver in each image at block 108 in FIG. 1 above.

In the block 302, the liver is separated from the heart in each image. Separating the liver and the heart in the images belonging to the native and the portal venous phases is necessary, because the liver and the heart have nearly the same intensity, so the result of the segmentation can include the heart. A method to eliminate this over-segmentation and exclude the heart from the liver, the liver-heart separation that takes into consideration that the right lung lobe contacts the top of the liver with a large surface is described in FIG. 4 below.

In segmentation of CT images, the intensity of the liver parenchyma is nearly homogeneous in each phase, so a region-growing method (RG) can effectively determine the liver volume. The segmentation for each phase consists of the following actions: First, an intensity range is determined, at block 304, which represents the liver in the given phase, based on voxels located in the ROI. Then, a region-growing is started from the voxels of the ROI at block 306. Finally, an additional segmentation is performed near the right lung lobe in order to reduce the under-segmentation of this region, at block 308.

In some embodiments, the intensity range of the liver cannot be perfectly determined. Extending the intensity range in order to avoid under-segmentation in one part of the liver can result over-segmentation in another part. In order to reduce the over-segmented regions, a neighborhood-connected RG process is applied. In a RG process, a voxel is added to the region if the local neighborhood of the voxel has acceptable intensity with some small tolerance. Using a larger neighborhood (sphere with 5 mm radius) which reduces the probability of over-segmentation without increasing the running time significantly.

Since the RG method uses a global intensity range, the liver is usually under-segmented near the right lung, where lower intensities can be found. This complication can be corrected by additional segmentation that uses lower intensity range in the region located between the segmented liver and right lung. The additional segmentation includes the following steps. First, (note, that the liver and the right lung lobe are already segmented), determining the surface of the right lung and the liver. Then the lung surface points are marked, which are located near the liver. Then, liver surface points are marked, which are located near the right lung. Then a closed 3D region is determined between the marked right lung and liver surface. Then a new intensity range of the liver is calculated based on this 3D region. Then, an additional region-growing is started from the liver surface points using this intensity range, which is limited to this 3D region.

Figure 4:
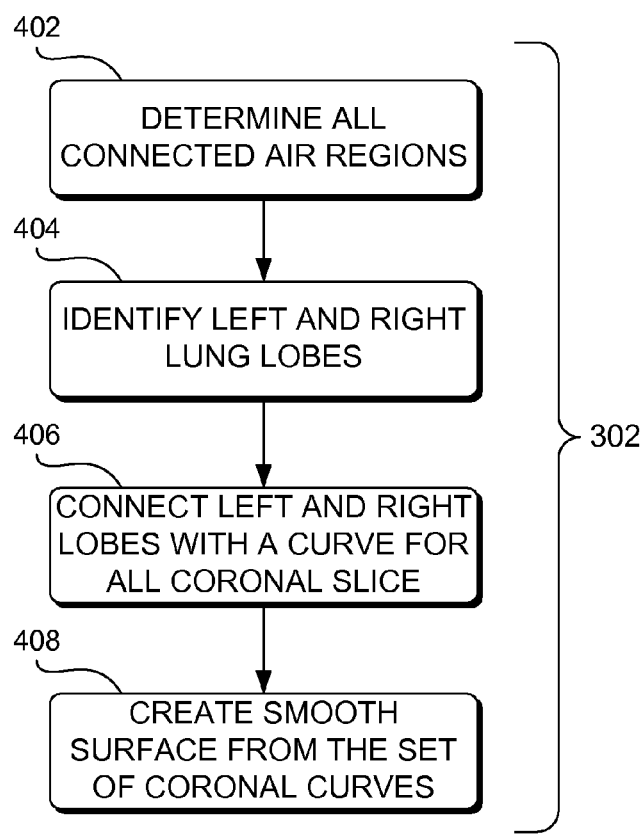
FIG. 4 is a flowchart of a process to separate the heart from the liver, according to an embodiment.

FIG. 4 is a flowchart of a process 400 to separate the heart from the liver, according to an embodiment. Process 400 is one example of separating the image of the heart from the image of the liver 302 in FIG. 3 above. In process 400, the heart and lung are separated using a smooth surface that fits the bottom of the left and right lung lobes and runs along high gradient values between the lobes.

Figure 6:
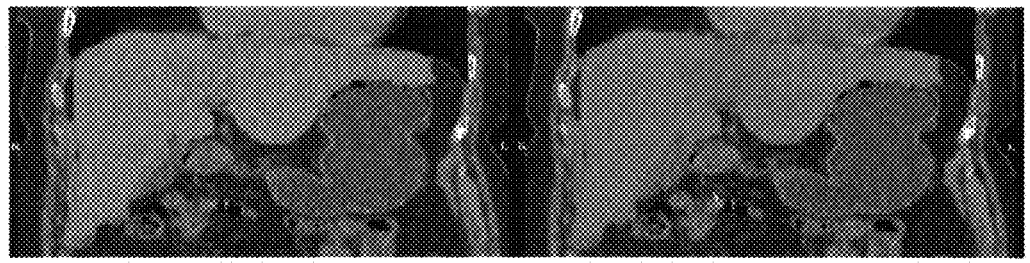
FIG. 6 shows the result of liver-heart separation, according to an embodiment.

In order to find the smooth surface, the left and right lung lobes are segmented. The segmentation starts with determining all connected air regions of the image, at block 402, which results in several connected air components. Then the lung lobes are identified based on the size and the spatial location of the largest connected air components, at block 404. After that, a minimal length curve is determined for all coronal slices, at block 406, which connects the left and right lung lobes and runs along high gradient values. When all slices are processed, a smooth surface is created from the set of coronal curves, at block 408. The smooth surface is used to prevent the segmentation to include the heart, as shown in FIG. 6 below.

Figure 5:
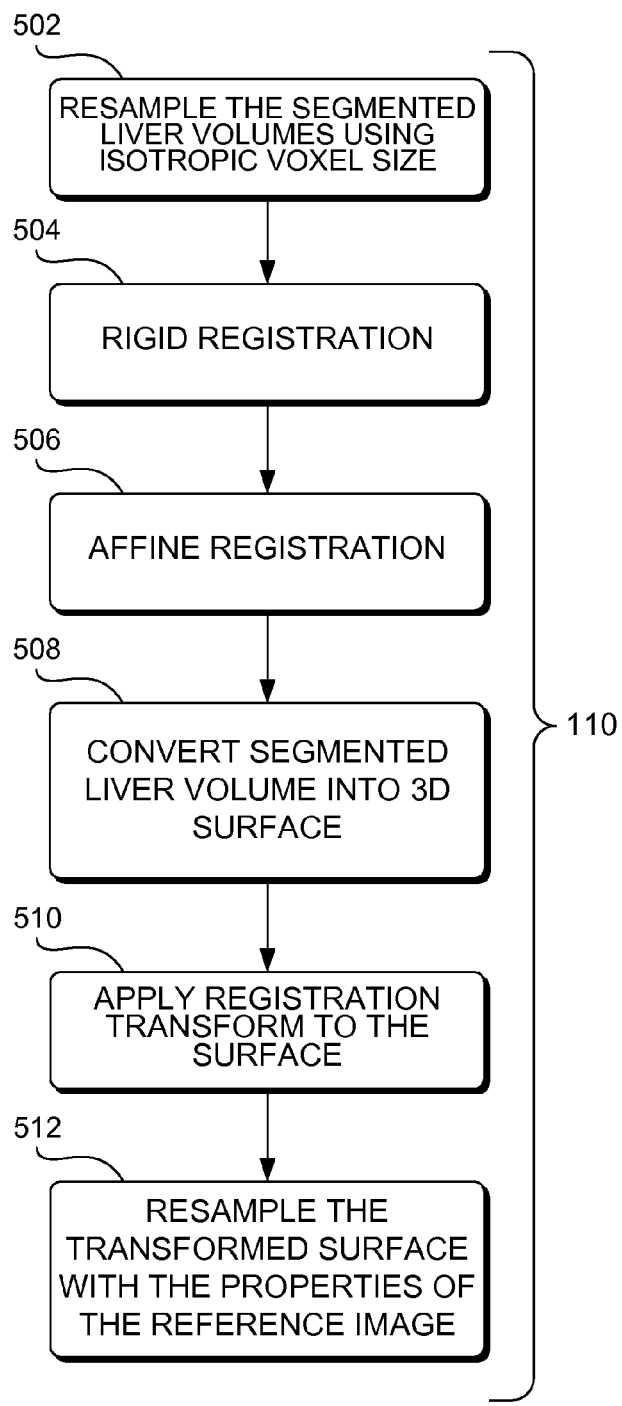
FIG. 5 is a flowchart of a process to register segmented images, according to an embodiment.

FIG. 5 is a flowchart of a process 500 to register segmented images, according to an embodiment. Process 500 is one example of registering segmented images 110 in FIG. 1 above.

Figure 9:
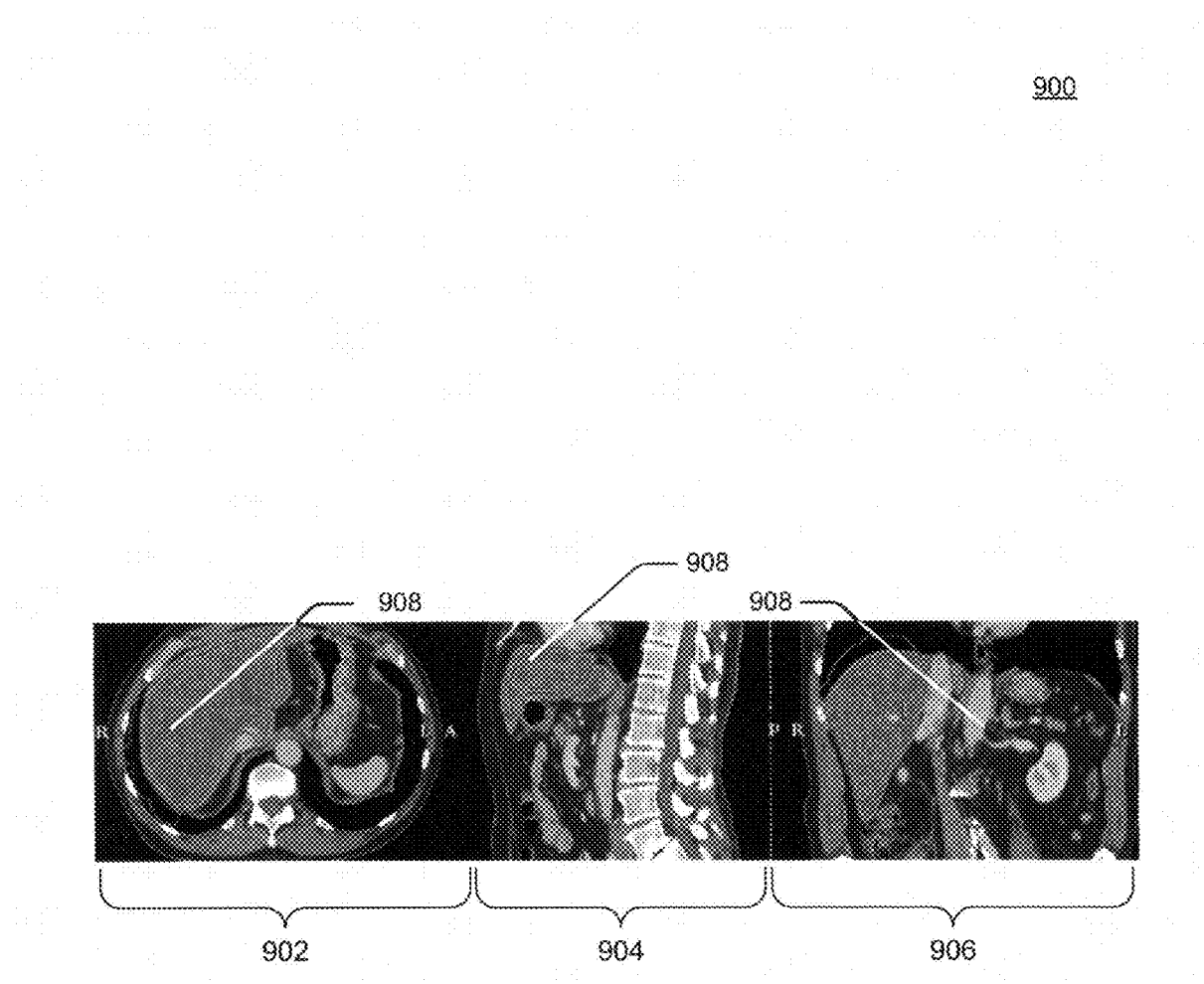
FIG. 9 shows an inter-phase registration problem, according to an embodiment.

The contrast agent is accumulated at different speed in the liver parenchyma as in the surrounding organs. Thus, in some embodiments, over-segmentation affects different parts of the liver at the different phases. Combining the segmentation results belonging to different phases can efficiently reduce the probability of such over-segmentations. Due to the patient's respiration the organs located close to the lung (e.g. the liver) can move/deform considerably from one phase to another (FIG. 9. depicts such a case). As shown in FIG. 9, that the liver is shifted down significantly due to respiration, especially on the coronal slices. To overcome this complication, the images belonging to the different phases can be registered. Registering different phases can be very time-consuming (some minutes per volume) for typical abdominal CT examinations. In order to reduce the running time, the registration can be performed only in the environment of the liver.

In the registration of segmented images, the segmented liver volumes are first resampled using isotropic voxel size (5×5×5 mm) before the registration starts, at block 502. Then, the registration is performed in 3D that includes two steps. First a translation is calculated, a rigid registration is performed, at block 504 and then an affine transform is determined, at block 506, such that the parameters of the affine transform namely the rotation/scale/shear matrix, the center of rotation, and the translation vector are initialized with the identity matrix, the weight center of the segmented liver, and the translation calculated in the first step, respectively. If the cost function, which is the square difference for sake of efficiency (but the cost function can be a more complex function), is not decreased in the second step, only the translation transform is used.

The segmented liver mask is displayed on the reference volume that is chosen by the user. In order to merge the different results, the registration transforms are applied to the segmented volumes, and the registered volumes are resampled to the original size and voxel spacing of the reference volume. This can be a very time consuming process. In order to save computation time, each segmented (binary) volume is converted into 3D triangle surface, at block 508, then the registration transform is applied to the surface, at block 510, and the transformed surface is resampled using the properties of the reference image, at block 512. Thus, the resampling concerns only the region of the liver, which saves a significant amount of time.

In the merging registered images, the segmented liver is available for all phases. Since the segmented images are registered, combining the information of the different images is possible. Combining the information of different images can be realized by defining a function, which assign to each voxel the probability of belonging to the liver. A simple function is the intersection, namely a given voxel is considered as a liver voxel, if the given belongs to the liver in all phases. This function can be more complex (incorporating the original grayscale image, the location of the voxel, etc.).

Images

FIG. 6 shows an image 600 of the result of liver-heart separation. As a result of the automatic separation of liver and heart, the segmentation result does not involve the heart.

Figure 7:
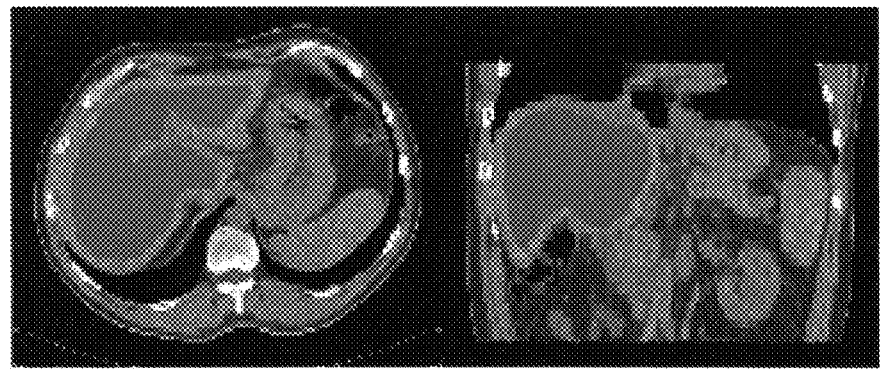
FIG. 7 shows an image after automatic liver region detection, according to an embodiment.

FIG. 7 shows an image 700 after automatic liver region detection. In FIG. 7, a relatively large connected volume inside the organ is identified.

Figure 8:
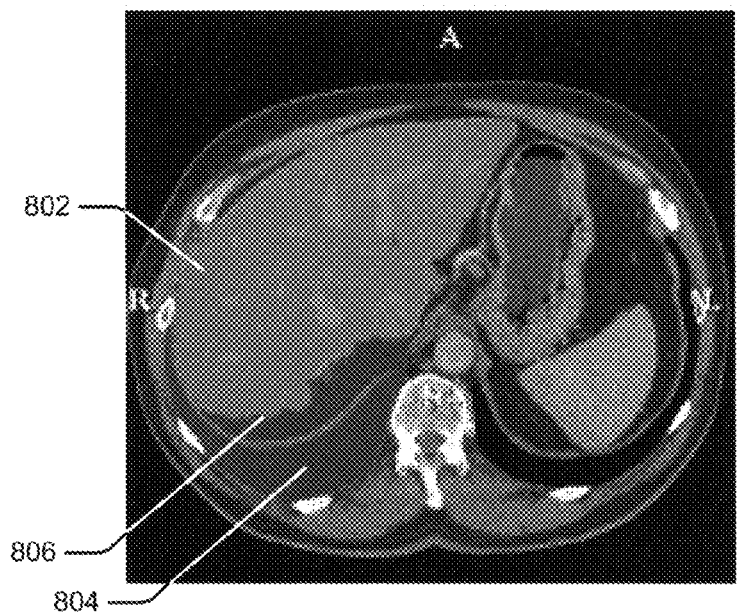
FIG. 8 shows additional segmentation near the right lung, according to an embodiment.

FIG. 8 shows an image 800 of additional segmentation near the right lung. The figure shows the result of the original segmentation (red region 802) is usually under-segmented near the right lung (green 804). Additional segmentation (blue 806) in the region located between the segmented liver and the right lung can reduce this under-segmentation.

FIG. 9 shows an image 900 of an inter-phase registration problem. The axial (left 902), sagittal (center 904), and coronal (right 906) slice of an image belonging to the portal venous phase. The green regions 908 represent the segmented liver volume belonging to this phase and the red contour shows the segmentation result belonging to the native phase. Due to respiration the position and the shape of the organ is so different that the two results cannot be combined without registration.

Histograms

FIGS. 10 through 13 illustrate images formed by combining multiple datasets and corresponding histograms, demonstrating the effects of varying degrees of registration. As is described below in more detail with reference to FIGS. 10 through 13 and associated text, identifying some features in images which are formed by combining two or more poorly registered datasets is possible.

Figure 10:
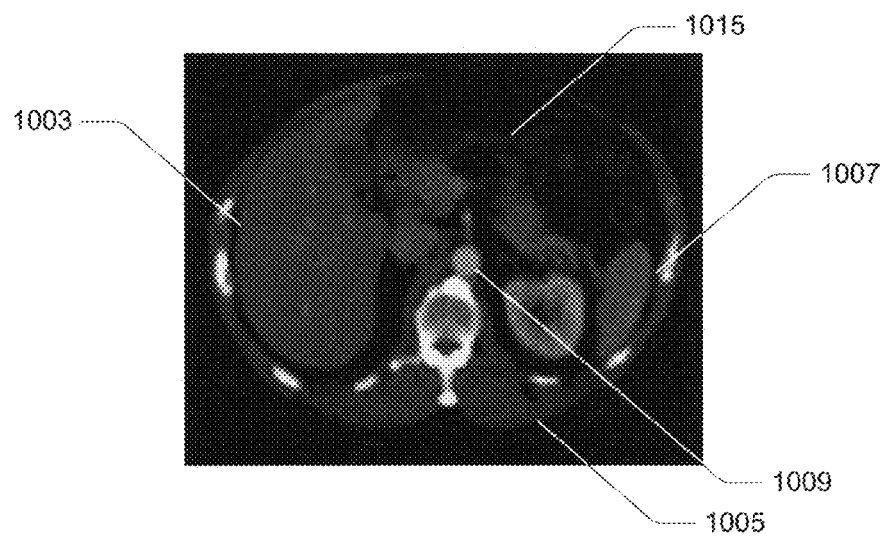
FIG. 10 includes an image formed by a registered combination of data from two phases, in accordance with an embodiment.
Figure 11:
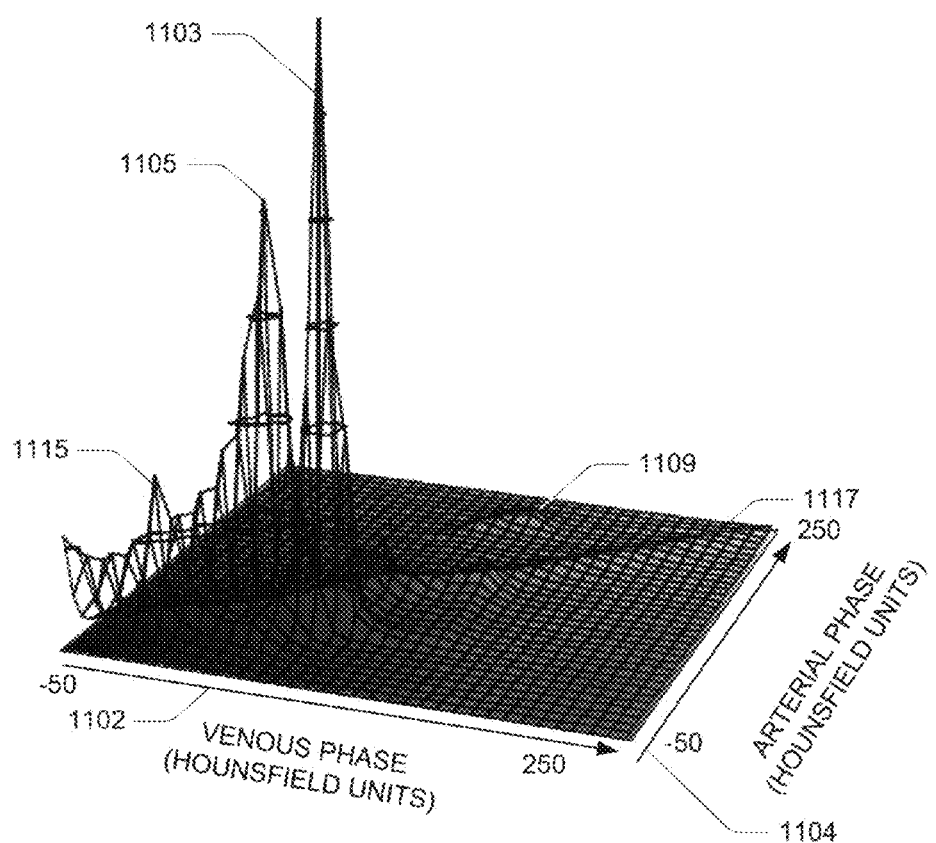
FIG. 11 shows a histogram corresponding to the image of FIG. 10, in accordance with an embodiment.

FIG. 10 includes an image 1000 formed by a registered combination of the arterial and portal venous phases of a contrast enhanced CT liver examination and FIG. 11 provides a corresponding two-phase histogram 1100, in accordance with an embodiment of the disclosed subject matter. The image 1000 includes an image of a liver 1003, musculature 1005, spleen 1007, artery 1009 and bowel 1015.

The two-phase histogram 1100 of FIG. 11 includes a first axis 1102, corresponding to the venous phase, a large peak 1103 which is the modus for the histogram 1100, and a second axis 1104, corresponding to the arterial phase. The first and second axes 1102 and 1104 are both calibrated in Hounsfield Units, over a range from −50 to 250. FIG. 11 also includes peaks 1105, 1109, 1115 and a clearly-defined diagonal peak 1117. The liver 1003 of FIG. 10 corresponds to the large peak 1103 in the histogram 1100 of FIG. 11. Each of the peaks 1105, 1109, 1115, etc. corresponds to a particular organ, in this instance, to the musculature 1005, arterial structure 1009 and bowel 1015, respectively.

Figure 12:
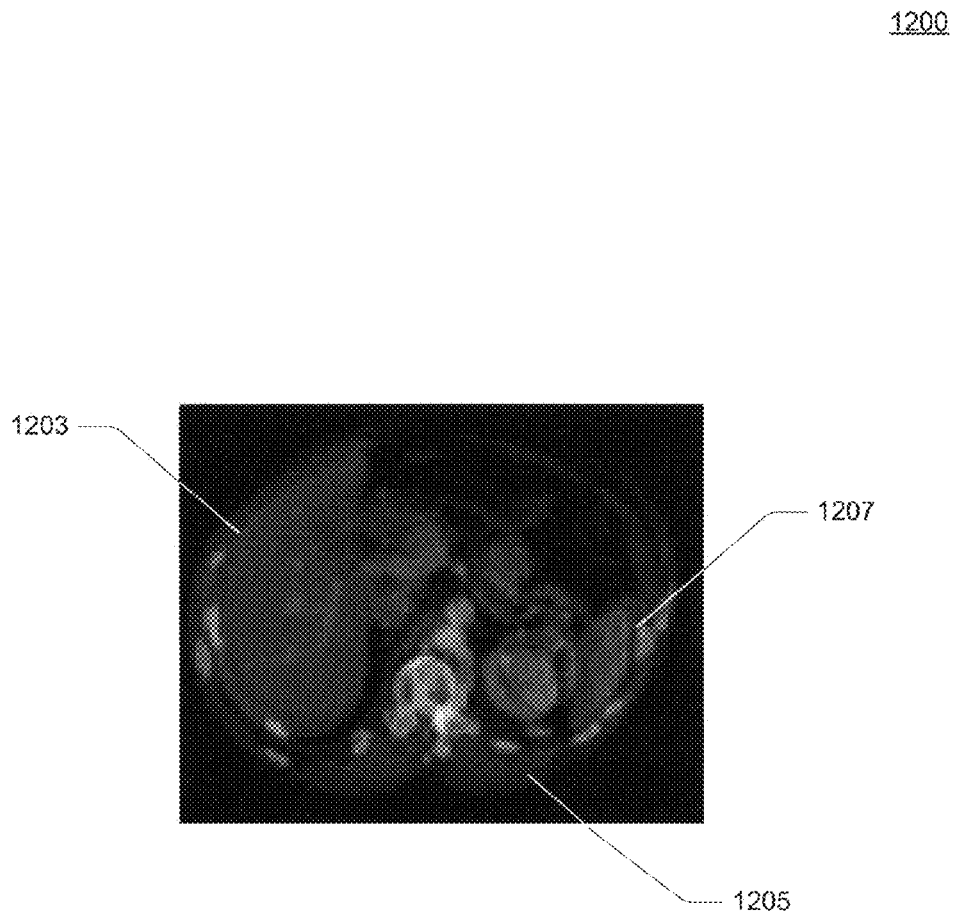
FIG. 12 includes an image formed by a poorly registered combination of two phases, in accordance with an embodiment.
Figure 13:
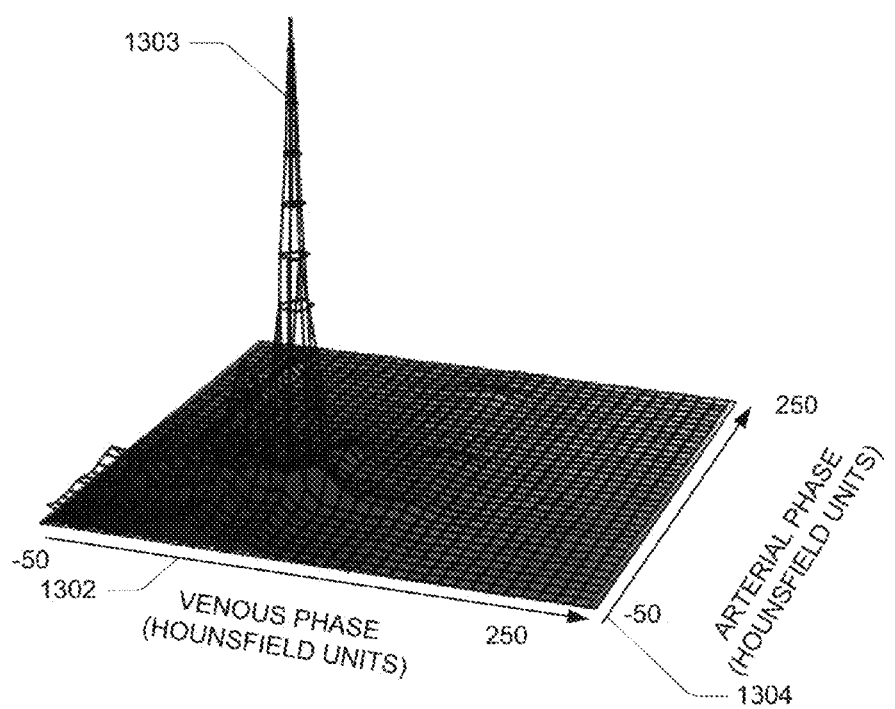
FIG. 13 shows a histogram corresponding to the image of FIG. 12, in accordance with an embodiment.

FIG. 12 includes an image 1200 formed by a roughly registered combination of the datasets for same two phases as used in FIGS. 10 and 11, and FIG. 13 is a histogram 1300 corresponding to the image 1200 of FIG. 12, in accordance with an embodiment of the disclosed subject matter. Rough registration may be accomplished using slice information such as is stored in the DICOM header associated with each dataset or image.

The histogram 1300 includes a first axis 1302, corresponding to the venous phase, a major peak 1303 or modus, and a second axis 1304, corresponding to the arterial phase. The first and second axes 1302 and 1304 are both calibrated in Hounsfield Units, over a range from −50 to 250.

When the different phases are only roughly registered, segmenting all the organs based on multiphase histogram analysis is difficult. The peak representing the liver is, however, still visible in the multiphase histogram due to the large volume of this organ. Thus, determining a relatively large region inside the liver (ROI) based on the multiphase histogram is possible.

Hardware and Operating Environment

Figure 14:
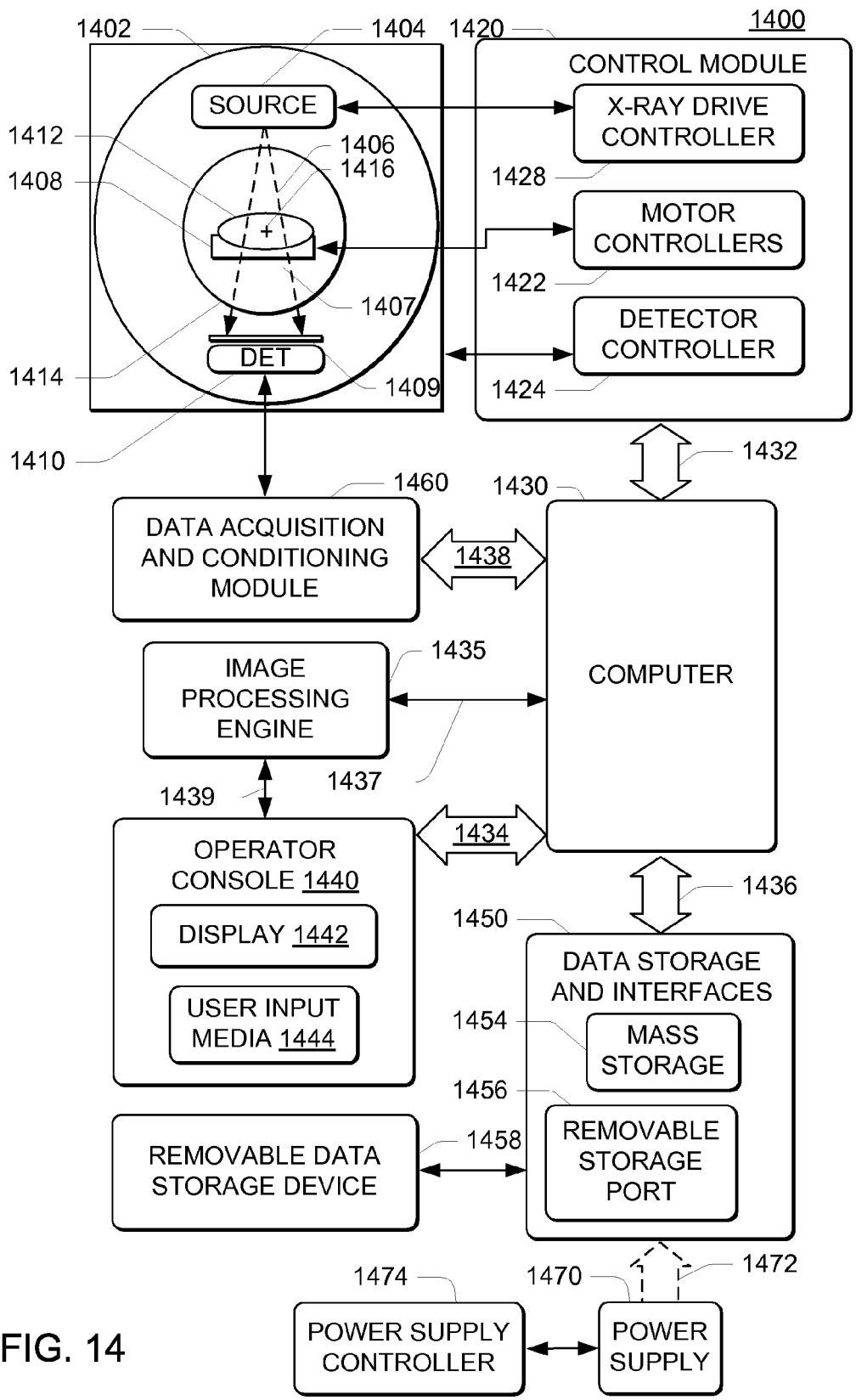
FIG. 14 is a block diagram of a system configured to provide and then enhance two- or three-dimensional anatomical data in conformance with one or more purpose-specific applications.

FIG. 14 is a simplified diagram of an overview of a modified system 1400 configured to improve X-ray imaging operations. The system 1400 optionally includes a gantry 1402 or other support for an illumination source 1404, such as an X-ray illumination source, capable of providing illumination 1406, such as X-rays or other non-destructive internal imaging illumination, and can optionally include a test subject support 1408 that is transmissive with respect to the illumination 1406 and that is positioned above a scintillator 1409 and detector 1410 that is also opposed to the illumination source 1404. Alternatively, a direct conversion detector 1410 can be employed without need for a scintillator.

In one embodiment, components of the system 1400 and a test subject 1412 are maintained in a defined geometric relationship to one another by the gantry 1402. A distance between the illumination source 1404 and the detector 1410 can be varied, depending on the type of examination sought, and the angle of the illumination 1406 respective to the test subject 1412 can be adjusted with respect to the body to be imaged responsive to the nature of imaging desired.

In one embodiment, the test subject support 1408 is configured to support and/or cause controlled motion of the test subject 1412, such as a living human or animal patient, or other test subject 1412 suitable for non-destructive imaging, above the scintillator 1409/detector 1410 so that illumination 1407 is incident thereon after passing through the test subject 1412. In turn, information from the detector array 1410 describes internal aspects of the test subject 1412.

The scintillator 1409 can be a conventional CsI scintillator 1409, optically coupled to an array of photodiodes (not illustrated), such as a two-dimensional array of photodiodes and suitable control transistors formed using semiconductor material such as amorphous silicon, or any other form of detector 1410 suitable for use with the type or types of illumination 1406 being employed, such as X-rays. The detector elements are typically tesselated in a mosaic. The scintillator 1409 converts incident photons comprising electromagnetic radiation, such as X-rays, from high-energy, high-frequency photons 1407, into lower-energy, lower-frequency photons corresponding to spectral sensitivity of the detector elements, in a fashion somewhat analogous to fluorescence, as is commonly known in the context of many visible-light sources in use today. Alternatively, the detector 1410 can be formed as a flat-panel array including amorphous Silicon (α-Si) active elements, together with either a scintillator layer 1409, or a direct converter material such as Cadmium Zinc Telluride (CdZnTe), Mercuric Iodide ($HgI_2$), Lead Iodide ($PbI_2$), or amorphous Selenium (α-Se).

In some modes of operation, such as CT, the gantry 1402 and test subject support or table 1408 cooperatively engage to move the test subject 1412 longitudinally within an opening 1414, that is, along an axis 1416 extending into and out of the plane of FIG. 14. In some modes of operation, the gantry 1402 rotates the X-ray source 1404 and detector 1410 about the axis 1416, while the support 1408 moves longitudinally, to provide a helical series of scans of the test subject 1412, where a pitch of the helices is defined as a ratio of a longitudinal distance traveled by the table 1408 during a complete revolution of the gantry 1402, compared to a length of the detector 1410 along the axis 1416 of linear motion.

The system 1400 also optionally includes a control module or controller 1420. The controller 1420 can include a motor control module 1422 configured to move the test subject support 1408 and thus the test subject 1412 relative to the X-ray source 1404 and/or detector 1410, and can also control motors in the gantry 1402 or to position the X-ray illumination source 1404 relative to the test subject 1412 and/or the detector 1410.

The controller 1420 includes a detector controller 1424 configured to control elements within the detector 1410 and to facilitate data transfer therefrom. The controller 1420 also includes a drive parameter controller 1428 configured to control electrical drive parameters delivered to the X-ray source 1404. One or more computers 1430 provide connections to the controller 1420 via a bus 1432 configured for receiving data descriptive of operating conditions and configurations and for supplying appropriate control signals. Buses 1434, 1437 and 1439 act to transfer data and control signals, for example with respect to a module 1435, configured as an image processing engine, via interconnections such as 1437, 1439 that are configured for exchange of signals and data to and/or from the computer 1430 as well as other elements of the system 1400 and/or external computation or communications resources (not illustrated in FIG. 14).

The system 1400 also includes a bus 1436, a bus 1438 and an operator console 1440. The operator console 1440 is coupled to the system 1400 through the bus 1434. The operator console 1440 includes one or more displays 1442 and a user input interface 1444. The user input interface 1444 can include a touchscreen, keyboard, a mouse or other tactile input device, capability for voice commands and/or other input devices. The one or more displays 1442 provide video, symbolic and/or audio information relative to operation of system 1400, user-selectable options and images descriptive of the test subject 1412, and can display a graphical user interface for facilitating user selection among various modes of operation and other system settings.

The image processing engine 1435 facilitates automation of accurate measurement and assessment. The image processing engine 1435 is capable of forming multiple, coordinated images for display, for example via the monitor 1442, to provide the types of depictions described below. The image processing engine 1435 can comprise a separate and distinct module, which can include application-specific integrated circuitry, or can comprise one or more processors coupled with suitable computer-readable program modules, or can comprise a portion of the computer 1430 or other computation device.

The system 1400 also includes memory devices 1450, coupled via the bus 1436 to the computer 1430 through suitable interfaces. Datasets representing three-dimensional data and image or two-dimensional data typically conform to the digital imaging and communications in medicine (DICOM) standard, which is widely adopted for handling, storing, printing, and transmitting information in medical imaging. The DICOM standard includes a file format definition and a network communications protocol. The communication protocol is an application protocol that uses TCP/IP to communicate between systems. DICOM files can be stored in memory devices 1450 and retrieved therefrom, and can be exchanged between two entities that are capable of receiving image and patient data in DICOM format.

The memory devices 1450 include mass data storage capabilities 1454 and one or more removable data storage device ports 1456. The one or more removable data storage device ports 1456 are adapted to detachably couple to portable data memories 1458, which can include optical, magnetic and/or semiconductor memories and can have read and/or write capabilities, and which can be volatile or non-volatile devices or can include a combination of the preceding capabilities.

The system 1400 further includes a data acquisition and conditioning module 1460 that has data inputs coupled to the detector 1410 and that is coupled by the bus 1438 to the one or more computers 1430. The data acquisition and conditioning module 1460 includes analog to digital conversion circuitry for capturing analog data from the detector 1410 and then converting those data from the detector 1410 into digital form, to be supplied to the one or more computers 1430 for ultimate display via at least one of the displays 1442 and for potential storage in the mass storage device 1454 and/or data exchange with remote facilities (not shown in FIG. 14). The acquired image data can be conditioned in either the data acquisition and conditioning module 1460 or the one or more computers 1430 or both.

The system 1400 also includes a power supply 1470, coupled via interconnections represented as a power supply bus 1472, shown in dashed outline, to other system elements, and a power supply controller 1474. In some embodiments, the system 1400 is configured to be a mobile system equipped with a portable power supply 1470, such as a battery. In other words, the system 1400 can comprise a wheeled unit and can be electromotively powered in self-contained fashion, lending physical agility to the ensemble of attributes offered by the system 1400.

Volumetric data collected via exposure of the test subject 1412 to suitable illumination 1406 can be processed via many different types of tools, each intended to enhance some portion of information content described by the data. One result can be inconsistency between analytical results from different types of signal processing tools, or between measurement results corresponding to different measurement times and/or measurement phases.

Figure 15:
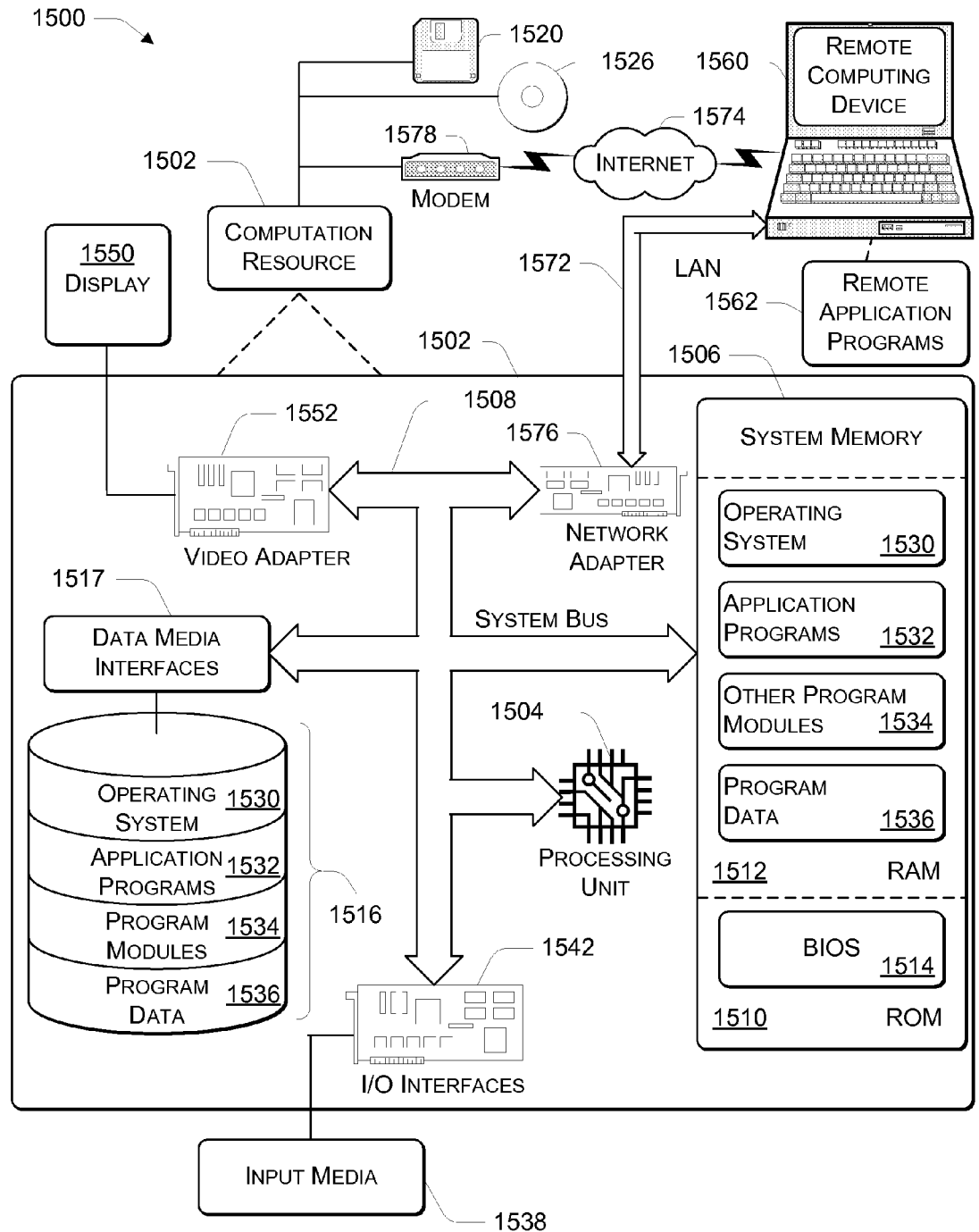
FIG. 15 illustrates an example of a general computation resource useful in the context of the environment of FIG. 14, in accordance with an embodiment.

FIG. 15 illustrates an example of a general computer environment 1500 useful in the context of the environment of FIG. 14, in accordance with an embodiment of the disclosed subject matter. The general computer environment 1500 includes a computation resource 1502 capable of implementing the processes described herein. It will be appreciated that other devices can alternatively used that include more components, or fewer components, than those illustrated in FIG. 15.

The illustrated operating environment 1500 is only one example of a suitable operating environment, and the example described with reference to FIG. 15 is not intended to suggest any limitation as to the scope of use or functionality of the embodiments of this disclosure. Other well-known computing systems, environments, and/or configurations can be suitable for implementation and/or application of the subject matter disclosed herein.

The computation resource 1502 includes one or more processors or processing units 1504, a system memory 1506, and a bus 1508 that couples various system components including the system memory 1506 to processor(s) 1504 and other elements in the environment 1500. The bus 1508 represents one or more of any of several types of bus structures, including a memory bus or memory controller, a peripheral bus, an accelerated graphics port and a processor or local bus using any of a variety of bus architectures, and can be compatible with SCSI (small computer system interconnect), or other conventional bus architectures and protocols.

The system memory 1506 includes nonvolatile read-only memory (ROM) 1510 and random access memory (RAM) 1512, which can or can not include volatile memory elements. A basic input/output system (BIOS) 1514, containing the elementary routines that help to transfer information between elements within computation resource 1502 and with external items, typically invoked into operating memory during start-up, is stored in ROM 1510.

The computation resource 1502 further can include a non-volatile read/write memory 1516, represented in FIG. 15 as a hard disk drive, coupled to bus 1508 via a data media interface 1517 (e.g., a SCSI, ATA, or other type of interface); a magnetic disk drive (not shown) for reading from, and/or writing to, a removable magnetic disk 1520 and an optical disk drive (not shown) for reading from, and/or writing to, a removable optical disk 1526 such as a CD, DVD, or other optical media.

The non-volatile read/write memory 1516 and associated computer-readable media provide nonvolatile storage of computer-readable instructions, data structures, program modules and other data for the computation resource 1502. Although the exemplary environment 1500 is described herein as employing a non-volatile read/write memory 1516, a removable magnetic disk 1520 and a removable optical disk 1526, it will be appreciated by those skilled in the art that other types of computer-readable media which can store data that is accessible by a computer, such as magnetic cassettes, FLASH memory cards, random access memories (RAMs), read only memories (ROM), and the like, can also be used in the exemplary operating environment.

A number of program modules can be stored via the non-volatile read/write memory 1516, magnetic disk 1520, optical disk 1526, ROM 1510, or RAM 1512, including an operating system 1530, one or more application programs 1532, other program modules 1534 and program data 1536. Examples of computer operating systems conventionally employed for some types of three-dimensional and/or two-dimensional medical image data include the NUCLEUS® operating system, the LINUX® operating system, and others, for example, providing capability for supporting application programs 1532 using, for example, code modules written in the C++® computer programming language.

A user can enter commands and information into computation resource 1502 through input devices such as input media 1538 (e.g., keyboard/keypad, tactile input or pointing device, mouse, foot-operated switching apparatus, joystick, touchscreen or touchpad, microphone, antenna etc.). Such input devices 1538 are coupled to the processing unit 1504 through a conventional input/output interface 1542 that is, in turn, coupled to the system bus. A monitor 1550 or other type of display device is also coupled to the system bus 1508 via an interface, such as a video adapter 1552.

The computation resource 1502 can include capability for operating in a networked environment (as illustrated in FIG. 14, for example) using logical connections to one or more remote computers, such as a remote computer 1560. The remote computer 1560 can be a personal computer, a server, a router, a network PC, a peer device or other common network node, and typically includes many or all of the elements described above relative to the computation resource 1502. In a networked environment, program modules depicted relative to the computation resource 1502, or portions thereof, can be stored in a remote memory storage device such as can be associated with the remote computer 1560. By way of example, remote application programs 1562 reside on a memory device of the remote computer 1560. The logical connections represented in FIG. 15 can include interface capabilities, e.g., such as interface capabilities 1452 (FIG. 14) a storage area network (SAN, not illustrated in FIG. 15), local area network (LAN) 1572 and/or a wide area network (WAN) 1574, but can also include other networks.

Such networking environments are commonplace in modern computer systems, and in association with intranets and the Internet. In certain embodiments, the computation resource 1502 executes an Internet Web browser program (which can optionally be integrated into the operating system 1530), such as the "Internet Explorer®" Web browser manufactured and distributed by the Microsoft Corporation of Redmond, Wash.

When used in a LAN-coupled environment, the computation resource 1502 communicates with or through the local area network 1572 via a network interface or adapter 1576. When used in a WAN-coupled environment, the computation resource 1502 typically includes interfaces, such as a modem 1578, or other apparatus, for establishing communications with or through the WAN 1574, such as the Internet. The modem 1578, which can be internal or external, is coupled to the system bus 1508 via a serial port interface.

In a networked environment, program modules depicted relative to the computation resource 1502, or portions thereof, can be stored in remote memory apparatus. It will be appreciated that the network connections shown are exemplary, and other means of establishing a communications link between various computer systems and elements can be used.

A user of a computer can operate in a networked environment 1400 using logical connections to one or more remote computers, such as a remote computer 1560, which can be a personal computer, a server, a router, a network PC, a peer device or other common network node. Typically, a remote computer 1560 includes many or all of the elements described above relative to the computer 1500 of FIG. 15.

The computation resource 1502 typically includes at least some form of computer-readable media. Computer-readable media can be any available media that can be accessed by the computation resource 1502. By way of example, and not limitation, computer-readable media can comprise computer storage media and communication media.

Computer storage media include volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, DVD, or other optical storage, magnetic cassettes, magnetic tape, magnetic disk storage or other magnetic storage devices, or any other media which can be used to store computer-intelligible information and which can be accessed by the computation resource 1502.

Communication media typically embodies computer-readable instructions, data structures, program modules or other data, represented via, and determinable from, a modulated data signal, such as a carrier wave or other transport mechanism, and includes any information delivery media. The term "modulated data signal" means a signal that has one or more of its characteristics set or changed in such a manner as to encode information in the signal in a fashion amenable to computer interpretation.

By way of example, and not limitation, communication media include wired media, such as wired network or direct-wired connections, and wireless media, such as acoustic, RF, infrared and other wireless media. The scope of the term computer-readable media includes combinations of any of the above.

The computer 1502 can function as one or more of the control segments of module 1420 (FIG. 14), the computer 1430, the operator console 1440 and/or the data acquisition and conditioning module 1460, for example, via implementation of the processes 100 and 400 of FIGS. 1 and 4, respectively, as one or more computer program modules.

Conclusion

Although specific embodiments have been illustrated and described herein, it will be appreciated by those of ordinary skill in the art that any arrangement which is calculated to achieve the same purpose can be substituted for the specific embodiments shown. This disclosure is intended to cover any adaptations or variations. For example, although described in procedural terms, one of ordinary skill in the art will appreciate that implementations can be made in a procedural design environment or any other design environment that provides the required relationships.

In particular, one of skill in the art will readily appreciate that the names or labels of the processes and apparatus are not intended to limit embodiments. Furthermore, additional processes and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types. The terminology used in this disclosure is meant to include all object-oriented, database and communication environments and alternate technologies which provide the same functionality as described herein.

What is claimed is:

1. A method comprising:
   receiving a plurality of images, each image including a liver and a heart;
   determining a liver region-of-interest in each of the images;
   segmenting a liver volume in each of the images;
   performing a second segmentation by applying a region-growing method to a region that is located between the segmented liver and a right lung;
   registering the segmented liver volumes generated based on the second segmentation; and
   combining all the registered liver volumes in a memory.

2. The method of claim 1, the method further comprising:
   merging the registered liver volumes to generate a plurality of merged images; and
   displaying the merged images.

3. The method of claim 1, wherein the determining the liver region-of-interest further comprises:
   creating a multiphase histogram of the received images;
   determining a maximum intensity value of the multiphase histogram;
   determining an intensity range of the liver for all received images;
   determining a set of potential liver voxels; and
   finding the largest connected region in the set of potential liver voxels.

4. The method of claim 1, wherein the segmenting the liver volume further comprises:
- separating the liver and the heart in each of the images;
- calculating an intensity range of the separated liver based on the liver region-of-interest;
- applying the region-growing method to the image.

5. The method of claim 4, wherein separating the liver and heart further comprises:
- determining at least one connected air region in the image, the connected air region including a plurality of connected air components;
- identifying the lung lobes, based on a spatial location of at least one of the connected air components;
- determining a minimal length curve for all coronal slices, which connects the left and right lung lobes and runs along high gradient values; and
- creating a smooth surface from the set of coronal curves.

6. The method of claim 1, wherein registering the segmented liver volumes further comprises:
- resampling the segmented liver volumes using isotropic voxel size;
- performing a three-dimensional rigid registration;
- performing a three-dimensional affine registration;
- converting each segmented binary volume into a three-dimensional triangle surface;
- applying registration transforms to the segmented volumes; and
- resampling the transformed surface using the properties of the reference image.

7. The method of claim 2, wherein merging the registered liver volumes comprises:
- calculating an image as an arbitrary function of the registered liver volumes and the received images.

8. The method of claim 1, wherein the plurality of images further comprise:
- a plurality of images acquired through multiphase contrast-enhanced computed tomography imaging.

9. A non-transitory computer-accessible medium having executable instructions to image a liver, the executable instructions capable of directing a processor to perform:
- receiving a plurality of images, each image including a liver and a heart;
- determining a liver region-of-interest in each of the images;
- segmenting a liver volume in each of the images;
- performing a second segmentation by applying a region-growing method to a region that is located between the segmented liver and a right lung;
- registering the segmented liver volumes generated based on the second segmentation; and
- combining all the registered liver volumes in a memory.

10. The non-transitory computer-accessible medium of claim 9, wherein the executable instructions capable of directing the processor to determine the liver region-of-interest further comprise executable instructions capable of directing the processor to perform:
- creating multiphase histogram of the received images;
- determining a maximum intensity value of the multiphase histogram;
- determining an intensity range of the liver for all received images;
- determining a set of potential liver voxels; and
- finding the largest connected region in the set of potential liver voxels.

11. The non-transitory computer-accessible medium of claim 9, the executable instructions further comprise:
- merging the registered liver volumes to generate a plurality of merged images; and
- displaying the merged images.

12. The non-transitory computer-accessible medium of claim 9, wherein the executable instructions capable of directing the processor to segment the liver volume further comprise executable instructions capable of directing the processor to perform:
- separating the liver and the heart in each of the images;
- calculating an intensity range of the liver based on the liver region-of-interest;
- applying the region-growing method to the image.

13. The non-transitory computer-accessible medium of claim 12, wherein the executable instructions capable of directing the processor to separate the liver and heart further comprise executable instructions capable of directing the processor to perform:
- determining at least one connected air region in the image, the connected air region including a plurality of connected air components;
- identifying the lung lobes, based on a spatial location of at least one of the connected air components;
- determining a minimal length curve for all coronal slices, which connects the left and right lung lobes and runs along high gradient values; and
- creating a smooth surface from the set of coronal curves.

14. The non-transitory computer-accessible medium of claim 9, wherein the executable instructions capable of directing the processor to register the segmented liver volumes further comprise:
- resampling the segmented liver volumes using isotropic voxel size;
- performing a three-dimensional rigid registration;
- performing a three-dimensional affine registration;
- converting each segmented binary volume into a three-dimensional triangle surface;
- applying registration transforms to the segmented volumes; and
- resampling the transformed surface using the properties of the reference image.

15. The non-transitory computer-accessible medium of claim 11, wherein the executable instructions capable of directing the processor to merge all registered liver volumes further comprise:
- calculating an image as an arbitrary function of the registered liver volumes and the received images.

16. A system comprising:
- a processor;
- a storage device coupled to the processor including a plurality of representations of multiphase contrast-enhanced computed-tomography images;
- software apparatus operative on the processor to receive a plurality of images, each image including a liver and a heart; to determine a liver region-of-interest in each of the images, to segment a liver volume in each of the images, to perform a second segmentation by applying a region-growing method to a region that is located between the segmented liver and a right lung; to register the segmented liver volumes generated based on the second segmentation, and combine all the registered liver volumes in a memory.

17. The system of claim 16, wherein the software apparatus to determine the liver region-of-interest in each of the images further comprises software apparatus operative on the processor to:
- create a multiphase histogram of the received images;

determine a maximum intensity value of the multiphase histogram;
determine an intensity range of the liver for all received images;
determine a set of potential liver voxels; and
find the largest connected region in the set of potential liver voxels.

18. The system of claim 16, wherein the software apparatus to segmenting the liver volume in each of the images further comprises software apparatus operative on the processor to:
separate the liver and the heart in each of the images,
calculate an intensity range of the liver based on the liver region-of-interest;
apply a region-growing method to the image; and
apply a region-growing method to a region that is located between the segmented liver and right lung.

19. The system of claim 18, wherein the software apparatus to separate the liver and the heart in each of the images further comprises software apparatus operative on the processor to:
determine at least one connected air region in the image, the connected air region including a plurality of connected air components;
identify the lung lobes, based on a spatial location of at least one of the connected air components;
determine a minimal length curve for all coronal slices, which connects the left and right lung lobes and runs along high gradient values; and
create a smooth surface from the set of coronal curves.

20. The system of claim 16, wherein the software apparatus to registering the segmented liver volumes further comprises software apparatus operative on the processor to:
resample the segmented liver volumes using isotropic voxel size;
perform a three-dimensional rigid registration;
perform a three-dimensional affine registration;
convert each segmented binary volume into three-dimensional triangle surface;
apply registration transforms to the segmented volumes; and
resample the transformed surface using the properties of the reference image.

* * * * *